United States Patent [19]

Kawai et al.

[11] 4,386,223

[45] May 31, 1983

[54] METHOD OF PURIFYING HEXAFLUOROACETONE CONTAINING CHLOROFLUOROACETONES

[75] Inventors: Toshikazu Kawai; Yutaka Maruyama, both of Kamifukuoka; Junji Negishi, Kawagoe; Akira Negishi, Sayama, all of Japan

[73] Assignee: Central Glass Company Limited, Ube, Japan

[21] Appl. No.: 320,079

[22] Filed: Nov. 10, 1981

[30] Foreign Application Priority Data

Nov. 11, 1980 [JP] Japan .................................. 55-157664

[51] Int. Cl.$^3$ .............................................. C07C 45/85
[52] U.S. Cl. .................................................. 568/411
[58] Field of Search ........................................... 568/411

[56] References Cited

U.S. PATENT DOCUMENTS

| | | | |
|---|---|---|---|
| 3,320,322 | 5/1967 | Langdon et al. | 568/411 |
| 3,433,838 | 3/1969 | Cunningham | 568/411 |
| 3,632,652 | 3/1968 | Chu et al. | 568/411 |
| 3,745,093 | 7/1973 | Lee | 568/411 |
| 4,059,633 | 11/1977 | Childs | 568/411 |

OTHER PUBLICATIONS

Krespan, J. Org. Chem., vol. 43, No. 4, pp. 637-640 (1978).

Primary Examiner—James H. Reamer
Attorney, Agent, or Firm—Fleit, Jacobson & Cohn

[57] ABSTRACT

Crude hexafluoroacetone (HFA) containing chlorofluoroacetone(s) (CFA) as well as hydrogen halide(s) is purified by initially allowing the crude HFA to be absorbed in water to give an aqueous solution in which HFA and CFA are in the form of their respective hydrates, adding a calcium compound such as carbonate, hydroxide or oxide to the solution to neutralize the hydrogen halide(s), and decomposing the hydrated CFA by first adding an alkali metal compound such as $K_2CO_3$ or $Na_2CO_3$ or an alkaline earth metal compound such as $Ca(OH)_2$, $Ba(OH)_2$, CaO or BaO to the solution and subsequently adding a mineral acid such as HCl or $H_2SO_4$ to the same solution. This procedure results in complete decomposition of CFA without causing decomposition of HFA and spontaneous separation of the liquid reaction system into two layers, one of which is exclusively HFA hydrate. Accordingly it is easy to separate pure HFA hydrate from the decomposed impurities.

6 Claims, No Drawings

METHOD OF PURIFYING HEXAFLUOROACETONE CONTAINING CHLOROFLUOROACETONES

BACKGROUND OF THE INVENTION

This invention relates to a method of purifying crude hexafluoroacetone which is obtained by reaction between hexachloroacetone and hydrogen fluoride and contains chlorofluoroacetones as well as hydrogen halides.

Hexafluoroacetone is useful as an intermediate of fluorine-containing polymers and some medicines and agricultural chemicals and also as a solvent for various polymeric materials.

As is well known, hexafluoroacetone can be prepared with fairly good yield by contact reaction between hexachloroacetone and anhydrous hydrogen fluoride in the presence of a suitable catalyst, for example a combination of chromium trifluoride and dichromium trioxide as disclosed in Japanese Patent Application Publication No. 40(1965)-27173. However, it is inevitable that the product of this reaction contains hydrogen chloride and/or hydrogen fluoride, and it is difficult to completely remove such hydrogen halides from the reaction product to thereby isolate hexafluoroacetone because each hydrogen halide readily combines with hexafluoroacetone to form a complex compound.

For example, Japanese Patent Application Publication No. 46(1971)-6761 proposes a complicated method of purifying crude hexafluoroacetone containing hydrogen halides. This method has the steps of preliminarily converting hydrogen fluoride in the crude material into hydrogen chloride, hydrating the crude material, removing a major portion of hydrogen chloride by heating, dehydrating the remaining hexafluoroacetone hydrate by using sulfuric acid, and finally making the dehydrated and accordingly gasified hexafluoroacetone contact with a neutralizing agent, which is a polybasic salt of either an alkali metal or an alkaline earth metal, in order to remove a trace amount of acidic impurity still present in the gaseous hexafluoroacetone. Besides the complicatedness of the procedure, it is a shortcoming of this method that removal of hydrogen fluoride which is usually contained in the crude material can be achieved only to a limited extent.

Other than the aforementioned hydrogen halides, some chlorofluoroacetones such as chloropentafluoroacetone, dichlorotetrafluoroacetone and trichlorotrifluoroacetone are usually present in a crude hexafluoroacetone obtained by reaction between hexachloroacetone and hydrogen fluoride. Unfortunately, it is quite difficult to separate these chlorofluoroacetones from hexafluoroacetone by distillation because these chlorofluoroacetones readily combine with the hydrogen halides similarly to hexafluoroacetone to form complex compounds. Moreover, some of these chlorofluoroacetones, e.g. chloropentafluoroacetone and dichlorotetrafluoroacetones, readily react with water analogously to hexafluoroacetone to form hydrates of various degrees of hydration, and the boiling points of stable hydrates of such chlorofluoroacetones and hexafluoroacetone are all within the narrow range from 105° to 106° so that it is impossible to separate hydrated hexafluoroacetone from the hydrates of the chlorofluoroacetone by distillation.

However, these chlorofluoroacetones (particularly chloropentafluoroacetone and dichlorotetrafluoroacetones) are highly toxic and therefore must completely be removed from hexafluoroacetone for use as an industrial material. Preferentially to physical separation methods such as distillation, there has been an eager demand for a good chemical process of completely decomposing such chlorofluoroacetones without decomposing hexafluoroacetone, but the demand has not yet been satisfied. A primary reason for the unsuccess is that both hexafluoroacetone and the chlorofluoroacetones are very high in reactivity. That is, hexafluoroacetone readily combines with an acidic compound such as a halogen-containing acid to form a complex compound and also readily reacts with an alkaline compound such as potassium hydroxide or sodium hydroxide to decompose into trifluromethane and a metal salt of trifluoroacetic acid. Besides, it readily reacts with various organic compounds, e.g. amines and alcohols. These chemical properties of hexafluoroacetone are almost similarly possesed by chlorofluoroacetones as homologeous compounds. Therefore, it has been accepted as quite difficult to separate chlorofluoroacetones from hexafluoroacetone by utilizing certain differences in chemical reactivities.

SUMMARY OF THE INVENTION

It is an object of the present invention to provide a novel method of purifying crude hexafluoroacetone containing at least one chlorofluoroacetone and probably at least one hydrogen halide, in which method the chlorofluoroacetone(s) can completely be decomposed whereas hexafluoroacetone remains undecomposed and can easily be separated from the decomposed impurities.

A method according to the invention for purification of a crude hexafluoroacetone containing the aforementioned impurities comprises the steps of: (a) allowing the crude hexafluoroacetone to be absorbed in water to give an aqueous solution in which hexafluoroacetone and the chlorofluoroacetone(s) are present in the form of their respective hydrates, (b) adding a calcium compound to the aqueous solution to neutralize the hydrogen halide(s) contained in the crude hexafluoroacetone, (c) decomposing the hydrated chlorofluoroacetone(s) present in the aqueous solution by first adding a decomposing agent selected from alkali metal carbonates, alkaline earth metal hydroxides and alkaline earth metal oxides to the aqueous solution and subsequently adding a mineral acid to the aqueous solution, and (d) separating hexafluoroacetone in the form of hydrate from the liquid reaction system after completion of the step (c) in a state spontaneously separated into two layers.

This invention is based on our discovery that chlorofluoroacetones such as chloropentafluoroacetone, dichlorotetrafluoroacetones and trichlorotrifluoroacetones contained in crude hexafluoroacetone can completely be decomposed by the above stated steps (a) and (c) without causing decomposition of hexafluoroacetone and that the liquid after this decomposition treatment spontaneously separates into two layers, one of which is purely hexafluoroacetone in the form of hydrate and the other contains the entire amounts of impurity compounds resulting from the decomposition of the chlorofluoroacetones.

Preferred examples of the calcium compound for use in the step (b) of the above stated method are $CaCO_3$, $Ca(OH)_2$ and $CaO$. Preferred examples of the decomposing agent for use in the step (c) are $K_2CO_3$, $Na_2CO_3$, $Ca(OH)_2$, $Ba(OH)_2$, CaO and BaO, and preferred examples of the mineral acid are anhydrous hydrogen chloride, hydrochloric acid and sulfuric acid. By using a suitable calcium compound such as $Ca(OH)_2$ or CaO, it is possible to perform the steps (b) and (c) simultaneously as a practically single step.

If desired, the final separation of the hydrated hexafluoroacetone may be preceded by the addition of a dehydrating agent such as $CaCl_2$ or its hydrate for the purpose of concentrating the hydrated hexafluoroacetone.

The purifying method according to the invention can easily be put into industrial practice and makes it possible to completely and reliably remove chlorofluoroacetones and hydrogen halides from crude hexafluoroacetone prepared by a conventional process. As additional advantages of this method from an industrial viewpoint, all the steps of this method can successively be performed at room temperature and within the same reaction vessel in which the reaction system remains in liquid phase over the entire stages, and the entire steps can be completed in a very short period of time. Besides, the purified hexafluoroacetone in the form of hydrate is quite easily separated from the decomposed impurities.

DESCRIPTION OF THE PREFERRED EMBODIMENTS

1. Hydration Step

In the practical sense, the first step of the method according to the invention is absorption of crude hexafluoroacetone which is gaseous at room temperature in water. The quantity of water for this purpose must be at least equivalent by mole to the total of hexafluoroacetone and differently halogenated acetones contained in the crude hexafluoroacetone. With a view to minimizing the loss of hexafluoroacetone, it is preferred that the mole ratio of water to hexafluoroacetone contained in the crude material is in the range from 3:1 to 100:1.

When absorbed in water, hexafluoroacetone and chlorofluoroacetones become their respective hydrates. It is known that hexafluoroacetone and chlorofluoroacetones can be hydrated to various degrees of hydration, respectively, as may generally be expressed by $HFA \cdot xH_2O$ and $CFA \cdot yH_2$ (wherein x and y are not necessarily integers), but in the present invention it is unnecessary to strictly limit the degrees of hydration, i.e. the values of x and y in these general formulas. Insofar as each of x and y in these formulas is not smaller than 1.0, the subsequent neutralizing and decomposing steps can be carried out smoothly and effectively.

2. Neutralization Step

At this step, hydrogen chloride and/or hydrogen fluoride usually contained in the crude hexafluoroacetone and hence in the aqueous solution obtained at the hydration step are neutralized by adding a suitable calcium compound, preferably $CaCO_3$, $Ca(OH)_2$ or CaO, to the aqueous solution. As to the quantity of the calcium compound used as the neutralizing agent, it suffices to use a theoretically needful quantity for neutralizing the total amount of hydrogen chloride and/or hydrogen fluoride present in the solution. However, the use of an excess amount of the neutralizing agent offers no problem because this agent does not cause decomposition of hexafluoroacetone. When $CaCO_3$ is employed as the neutralizing agent there occurs bubbling of carbon dioxide gas in the solution, but this offers no problem. Whether carbon dioxide is evolved or not, the liquid reaction system after completion of this neutralizing step separates into two layers, and hexafluoroacetone and chlorofluoroacetones are all present exclusively in the lower one of the two layers.

3. Decomposition Step

A selected decomposing agent is added to the crude hexafluoroacetone solution after the above described neutralizing treatment (in the state as separated into two layers, or optionally preceded by removal of the upper layer) until the pH of the solution exceeds 7.0 to thereby cause decomposition of the chlorofluoroacetones. It is preferred to use $K_2CO_3$, $Na_2CO_3$, $Ca(OH)_2$, $Ba(OH)_2$, CaO or BaO as the decomposing agent. If desired, either of the alkali metal carbonates and one of the alkaline earth metal compounds may be used jointly. As mentioned hereinbefore, the above described neutralization step and this decomposition step can be united into a single step by using either $Ca(OH)_2$ or CaO as the neutralizing and decomposing agent. It suffices that the quantity of the decomposing agent is equivalent by mole to the total quantity of hexafluoroacetone and chlorofluoroacetones contained in the solution, but the use of an excess quantity of the decomposing agent offers no problem because this agent does not cause decomposition of hexafluoroacetone.

Next, the alkalinized reaction system is again neutralized by the addition of a mineral acid such as anhydrous hydrogen chloride, hydrochloric acid or sulfuric acid. It suffices that the quantity of the mineral acid is equivalent to the precedently added decomposing agent.

The selection of the decomposing agent and the selection of the mineral acid can be made independently, but it is very preferable to use either $Ca(OH)_2$ or CaO as the decomposing agent in combination with either anhydrous hydrogen chloride or hydrochloric acid.

Upon completion of this treatment the liquid reaction system separates spontaneously into two layers, the lower one of which is exclusively hexafluoroacetone hydrate.

The decomposition reactions at this step are represented by the following equations with respect to the treatment of crude hexafluoroacetone containing chloropentafluoroacetone with $K_2CO_3$ and HCl by way of example.

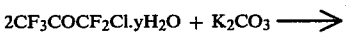

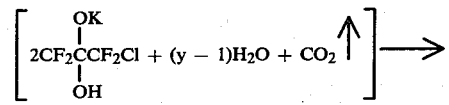

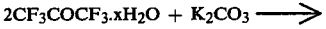

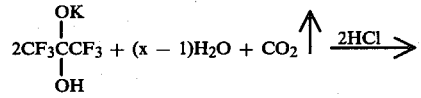

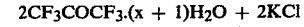

It is possible to obtain a pure hexafluoroacetone hydrate by distillation of the liquid reaction system in the state as separated into two layers or after a separation procedure to remove the upper layer. If desired, however, the hydrated hexafluoroacetone in the lower layer of the separated liquid may be concentrated by the following treatment before distillation.

4. Concentrating Step

This step is the addition of either $CaCl_2$ or its hydrate having dehydrating ability to the liquid remaining after completion of the above described decomposition step. This treatment results in clearer separation of the liquid into two layers and a decrease in the proportion of water to hexafluoroacetone in the lower layer.

A suitable quantity of the dehydrating agent varies depending on the composition of the liquid reaction system, and it is undesirable to use an unnecessarily large amount of the dehydrating agent because it will increase the loss of hexafluoroacetone. It is suitable that the mole ratio of the dehydrating agent to free water in the solution of hexafluoroacetone hydrate falls in the range from about 0.0005 to about 0.5. The distribution coefficient of hexafluoroacetone between the aforementioned two layers somewhat varies depending on the quantity of the dehydrating agent. For example, when 0.1 mole of $CaCl_2$ is used per mole of free water in the reaction system, the recovery of hexafluoroacetone reaches 99% or above. By using a larger quantity of $CaCl_2$, it is possible to further (but slightly) increase the recovery of hexafluoroacetone, i.e. percentage of hexafluoroacetone retained in the lower layer of the separated liquid reaction system. The use of a smaller amount of the dehydrating agent tends to cause a slight decrease in the recovery of hexafluoroacetone but may be practiced with a view to desirably controlling the degree of hydration of hexafluoroacetone hydrate (the value of x in the general formula $(CF_3)_2CO \cdot xH_2O$) in the aqueous solution.

Whether the concentrating step is added or not, the decomposition products of chlorofluoroacetones such as haloganated methanes, perhalogenated acetic acids and metal salts of perhalogenated acetic acids are entirely present in the upper one of the two liquid layers without entering the lower layer.

5. Dehydration Step

A high purity hexafluoroacetone hydrate obtained by the purifying method according to the invention can easily be dehydrated into high purity hexafluoroacetone by using a popular dehydrating or drying agent such as concentrated sulfuric acid, $P_2O_5$ or $SO_3$.

Every step of the purifying method of the invention can be performed at room temperature, so that there is no need of particularly heating or cooling the reaction system. Throughout the entire steps, pressure is not a matter of importance so that the entire process can be performed at the atmospheric pressure.

In the present invention it is particularly preferred to use $Ca(OH)_2$ as the calcium compound in the neutralizing step and also as the decomposing agent in the next step and select HCl as the mineral acid in the decomposing step, partly because of the formation of $CaCl_2$ which reduces the need or load of the optional concentrating step.

The following examples are presented to illustrate the purifying method according to the invention. Needless to mention, these examples are by no means limitative of the invention.

EXAMPLE 1

Crude hexafluoroacetone as a gaseous product of a catalytic reaction between hexachloroacetone and hydrogen fluoride gas was allowed to be absorbed in water to give an aqueous solution of the following composition.

Hexafluoroacetone—0.95 moles
Chloropentafluoroacetone—0.045 moles
Dichlorotetrafluoroacetones—0.015 moles
Hydrogen chloride—0.91 moles
Hydrogen fluoride—0.21 moles
Water—10.49 moles As a matter of course, hexafluoroacetone and the chlorofluoroacetones in this solution were in the form of hydrates.

With stirring, 1.65 moles of $Ca(OH)_2$ was added to this aqueous solution, and thereafter stirring was continued for a period of 10 min. This treatment was for the purpose of neutralizing the hydrogen halides and simultaneously decomposing the chlorofluoroacetones. After this treatment, the pH of the solution was about 11.

Then, the alkalinized solution was again neutralized by the addition of 2.18 moles of hydrogen chloride. As a result, the liquid reaction system separated into two liquid layers. The lower liquid layer was separated from the upper layer and confirmed to be an aqueous solution of the following composition.

Hexafluoroacetone—0.942 moles
Water—2.850 moles

In this aqueous solution the mole ratio of hexafluoroacetone to water was 1:3.03, indicating that a hexafluoroacetone hydrate expressed by $(CF_3)_2CO \cdot 3H_2O$ was isolated from the crude material. The recovery of hexafluoroacetone was calculated to be 99.2%. The content of HCl and HF in this hydrate was analyzed by the chlorine ion and fluorine ion electrode method and the content of chloropentafluoroacetone and dichlorotetrafluoroacetones by gas chromatography, but both were below the minimum concentrations required for quantitative analysis. This means that practically 100% removal of these impurities was achieved.

EXAMPLE 2

Crude hexafluoroacetone as a gaseous product of a usual synthesis process was allowed to be absorbed in water to give an aqueous solution of the following composition.

Hexafluoroacetone—1.03 moles
Chloropentafluoroacetone—0.52 moles
Dichlorotetrafluoroacetones—0.10 moles
Trichlorotrifluoroacetones—0.02 moles
Hydrogen chloride—3.60 moles
Water—11.26 moles Stirring this solution, 1.82 moles of $CaCO_3$ was added to the solution to neutralize HCl contained in the solution. Thereafter, 1.0 mole of $CaCl_2 \cdot 2H_2O$ was added to the solution to result in that the solution separated into two liquid layers.

After separation and abandonment of the upper liquid layer, 0.95 moles of $K_2CO_3$ was added to the solution left as the lower layer, with stirring, in order to decompose chlorofluoroacetones. By this treatment the pH of the solution became 10.8. Immediately thereafter, the solution was again neutralized by the addition of concentrated hydrochloric acid (0.52 moles as HCl), followed by the addition of 0.35 moles of $CaCl_2 \cdot 2H_2O$. The thus treated liquid separated into two liquid layers, and it was confirmed that in the lower layer the mole ratio of hexafluoroacetone to water was 1:5.02. Further addition of 0.18 moles of $CaCl_2 \cdot 2H_2O$ to the two-layer liquid resulted in that the mole ratio of hexafluoroacetone to water in the lower layer was concentrated to the extent of 1:3.0. The lower layer was separated from the upper layer and confirmed to be a colorless solution of the following composition.

Hexafluoroacetone—0.99 moles
Water—2.97 moles

This solution was dropped onto 500 g of concentrated sulfuric acid for the purpose of dehydration, and hexafluoroacetone gas evolved by this procedure was collected in a trap cooled with dry ice to thereby recover purified anhydrous hexafluoroacetone. In this example the recovery of hexafluoroacetone reached 96.1%, and practically 100% removal was achieved with respect to each of hydrogen chloride, chloropentafluoroacetone, dichlorotetrafluoroacetones and trichlorotrifluoroacetone contained in the crude material.

EXAMPLE 3

Crude hexafluoroacetone as a gaseous product of a usual synthesis process was subjected to a known treatment for removal of major portions of hydrogen halides and thereafter allowed to be absorbed in water to give an aqueous solution of the following composition.

Hexafluoroacetone—1.60 moles
Chloropentafluoroacetone—0.052 moles
Dichlorotetrafluoroacetones—0.002 moles
Hydrogen chloride—0.040 moles
Water—3.80 moles Stirring this solution, 1.65 moles of $Ca(OH)_2$ was added to the solution in order to neutralize hydrogen chloride and to simultaneously decompose the chlorofluoroacetones, and thereafter stirring was continued for a period of 5 min. After this treatment, the pH of the liquid reaction system was about 10. Next, the alkalinized liquid reaction system was neutralized by the addition of concentrated hydrochloric acid (1.60 moles as HCl) with the result that the liquid reaction system separated into two layers. The lower layer was separated from the upper layer and confirmed to be an aqueous solution of the following composition.

Hexafluoroacetone—1.56 moles
Water—5.21 moles

This solution was dropped onto 1000 g of concentrated sulfuric acid, and hexafluoroacetone gas evolved by this procedure was collected in a trap cooled with dry ice to thereby recover purified and anhydrous hexafluoroacetone. In this example the recovery of hexafluoroacetone was calculated to be 97.5%, and practically 100% removal of chloropentafluoroacetone, dichlorotetrafluoroacetones and hydrogen chloride was achieved.

EXAMPLE 4

Crude hexafluoroacetone as a gaseous product of a usual synthesis process was subjected to a known treatment for removal of major portions of hydrogen halides and thereafter allowed to be absorbed in water to give an aqueous solution of the following composition.

Hexafluoroacetone—1.60 moles
Chloropentafluoroacetone—0.052 moles
Dichlorotetrafluoroacetones—0.002 moles
Hydrogen chloride—0.040 moles
Water—3.80 moles Stirring this solution, 1.65 moles of $Ca(OH)_2$ was added to the solution as a neutralizing and decomposing agent, and stirring was continued for 5 min thereafter. After this treatment, the pH of the solution was about 10. The alkalinized reaction system was neutralized by the addition of 0.80 moles of concentrated sulfuric acid. After that, the addition of 0.5 moles of $CaCl_2$ caused the liquid reaction system to separate into two layers. The lower liquid layer was separated from the upper layer and confirmed to be an aqueous solution of the following composition.

Hexafluoroacetone—1.55 moles
Water—4.40 moles

In this solution the mole ratio of hexafluoroacetone to water was 1:2.84. In this example, the recovery of hexafluoroacetone was calculated to be 96.9%, and practically 100% removal of chloropentafluoroacetone, dichlorotetrafluoroacetones and hydrogen chloride was achieved.

What is claimed is:

1. A method of purifying crude hexafluoroacetone containing at least one chlorofluoroacetone or a mixture containing at least one chlorofluoroacetone and at least one hydrogen halide, the method comprising the steps of:
   (a) allowing the crude hexafluoroacetone to be absorbed in water to give an aqueous solution in which hexafluoroacetone and said at least one chlorofluoroacetone are present in the form of their respective hydrates wherein the ratio of water to the total of hexafluoroacetone and said at least one chlorofluoroacetone in said crude hexafluoroacetone is in the range of 3:1 to 100:1;
   (b) adding a calcium compound selected from the group consisting of $CaCO_3$, $Ca(OH)_2$ and CaO to said aqueous solution to neutralize said at least one hydrogen halide;
   (c) decomposing the hydrate of each of said at least one chlorofluoroacetone by first adding a molar equivalent of a decomposing agent based on the total quantity of hexafluoroacetone and said at least one chlorofluoroacetone present in said solution, wherein said decomposing agent is selected from the group consisting of alkali metal carbonates, alkaline earth metal hydroxides and alkaline earth metal oxides, to said aqueous solution and subsequently adding a mineral acid selected from the group consisting of anhydrous hydrogen chloride, hydrochloric acid and sulfuric acid to said aqueous solution in a quantity sufficient to neutralize said decomposing agent;
   (d) providing $CaCl_2$ or a hydrate thereof in the aqueous solution, thereby partially dehydrating the reaction system and consequently concentrating hexafluoroacetone in the form of a hydrate; and
   (e) separating hexafluoroacetone in the form of hydrate from the liquid reaction system after completion of step (d) wherein the solution spontaneously separates into two layers.

2. A method according to claim 1, wherein said decomposing agent is selected from the group consisting of $K_2CO_3$, $Na_2CO_3$, $Ca(OH)_2$, $Ba(OH)_2$, CaO and BaO.

3. A method according to claim 2, wherein said calcium compound and said decomposing agent are the same compound, so that the steps (b) and (c) are performed substantially simultaneously.

4. A method according to claim 3, wherein said calcium compound and said decomposing agent are both $Ca(OH)_2$, said mineral acid being selected from the group consisting of anhydrous hydrogen chloride and hydrochloric acid.

5. A method according to claim 1, wherein step (d) is performed by adding $CaCl_2$ or a hydrate thereof to the liquid reaction system after the step (c) but before the step (e) thereby concentrating hexafluoroacetone in the form of hydrate.

6. A method according to claim 1, wherein the mole ratio of said $CaCl_2$ or hydrate thereof to free water in said liquid reaction system is in the range from 0.0005 to 0.5.

* * * * *